US010261298B1

United States Patent
Hong et al.

(10) Patent No.: US 10,261,298 B1
(45) Date of Patent: Apr. 16, 2019

(54) NEAR-INFRARED-II CONFOCAL MICROSCOPE AND METHODS OF USE

(71) Applicant: The Board of Trustees of the Leland Stanford Junior University, Stanford, CA (US)

(72) Inventors: Guosong Hong, Somerville, MA (US); Alexander Antaris, Stanford, CA (US); Shuo Diao, Jilin (CN); Hongjie Dai, Cupertino, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 256 days.

(21) Appl. No.: 14/962,988

(22) Filed: Dec. 8, 2015

Related U.S. Application Data

(60) Provisional application No. 62/089,622, filed on Dec. 9, 2014.

(51) Int. Cl.
  *G02B 21/06* (2006.01)
  *G02B 21/00* (2006.01)
  (Continued)

(52) U.S. Cl.
  CPC ....... *G02B 21/0076* (2013.01); *C12Q 1/6816* (2013.01); *G01N 21/6428* (2013.01);
  (Continued)

(58) Field of Classification Search
  CPC .. G02B 21/00; G02B 21/0012; G02B 21/002; G02B 21/0024; G02B 21/0032;
  (Continued)

(56) References Cited

U.S. PATENT DOCUMENTS

| 5,880,880 A | 3/1999 | Anderson et al. |
| 6,208,886 B1 * | 3/2001 | Alfano ................. A61B 5/0073 |
| | | 250/341.1 |

(Continued)

FOREIGN PATENT DOCUMENTS

WO 02073246 A2 9/2002

OTHER PUBLICATIONS

Diao, S., et al., "Fluorescence Imaging In Vivo at Wavelengths beyond 1500 nm," Angewandte Chemie (2015) 127:14971-14975.
(Continued)

*Primary Examiner* — Thong Q Nguyen
(74) *Attorney, Agent, or Firm* — Brian E. Davy; Bozicevic, Field & Francis LLP

(57) ABSTRACT

Disclosed are methods and devices for confocal microscopy in the near-infrared. wavelength. The device uses a near-infrared (NIR) light producing source such as laser; optical components designed to reflect and transmit NIR from a sample; and an NIR detector coupled to a computer for constructing a focal plane image from a raster scan. The detector may be a photodiode or photo-multiplier tube for detecting fluorescence signals in the NIR (800-1700 nm) wavelength range using a variety of NIR-I (800-1000 nm) and NIR-II (1000-1700 nm) dyes and nanomaterials. An imaging method is described using the NIR-confocal microscope for slice by slice 3D imaging of biological tissues throughout a thickness up to, for example, 5 mm in the NIR-II window. The reduced scattering in NIR-II allows for tissue penetration up to about 5-10 mm, superior to ~0.2 mm afforded by conventional imaging.

23 Claims, 10 Drawing Sheets

(51) Int. Cl.
*G01N 21/64* (2006.01)
*C12Q 1/6816* (2018.01)

(52) U.S. Cl.
CPC ..... *G01N 21/6458* (2013.01); *G01N 21/6486* (2013.01); *G02B 21/0032* (2013.01); *G02B 21/0036* (2013.01); *G01N 2021/6439* (2013.01); *G01N 2223/509* (2013.01)

(58) Field of Classification Search
CPC ............ G02B 21/0036; G02B 21/0052; G02B 21/006; G02B 21/0076; G02B 21/008; G02B 21/0084; G02B 21/06; G02B 21/26; G01N 21/00; G01N 21/21; G01N 21/658; A61B 5/0075; A61B 5/0086
See application file for complete search history.

(56) References Cited

U.S. PATENT DOCUMENTS

| | | | |
|---|---|---|---|
| 6,734,962 | B2 | 5/2004 | Treado et al. |
| 7,042,556 | B1* | 5/2006 | Sun .................. G01N 21/21 356/237.1 |
| 8,060,187 | B2* | 11/2011 | Marshik-Geurts ... A61B 5/0086 600/473 |
| 8,679,426 | B2* | 3/2014 | Barrett .................. G01N 33/84 422/550 |
| 2007/0057211 | A1* | 3/2007 | Bahlman ............ G01N 21/6452 250/584 |
| 2009/0166560 | A1* | 7/2009 | Dai ......................... B82Y 5/00 250/492.1 |
| 2009/0273782 | A1* | 11/2009 | Yoo ....................... B23K 26/03 356/318 |
| 2011/0204258 | A1 | 8/2011 | Heller et al. |
| 2013/0172220 | A1* | 7/2013 | Ruhe, Jr. ............... C10M 133/54 508/238 |
| 2013/0230464 | A1 | 9/2013 | Yi et al. |
| 2014/0079630 | A1 | 3/2014 | Smith et al. |
| 2014/0113283 | A1* | 4/2014 | Suh ..................... G01N 21/658 435/6.1 |
| 2016/0178439 | A1* | 6/2016 | Freudiger ................ G01J 3/44 356/301 |

OTHER PUBLICATIONS

Diao, S., et al., "Biological imaging without autofluorescence in the second near-infrared region," Nano Research (2015) 8(9):3027-3034.

Hong, G., et al., "Multifunctional in vivo vascular imaging using near-intrared II fluorescence," Nature Medicine (2012) 18:1841-1846.

Hong, G., et al., "Near-Infrared II Fluorescence for Imaging Hindlimb Vessel Regeneration with Dynamic Tissue Perfusion Measurement," Circ. Cardiovasc. Imaging (2014) 7(3):517-525.

Köklü, F.H., et al., "Subsurface Imaging with Widefield and Confocal Numerical Aperture Increasing Lens Microscopes," Proceedings of the 19th Annual Meeting of the IEEE (2006) pp. 695-696.

Liu, J.T.C., et al., "Miniature near-infrared dual-axes confocal microscope utilizing a two-dimensional microelectromechanical systems scanner," Opt. Lett. (2007) 32(3): 256-258.

Loterie, D., et al., "Digital confocal microscopy through a multimode fiber," Optics express (2015) 23(18): 23845-23858.

Nehal, K.S., et al., "Skin Imaging With Reflectance Confocal Microscopy," Semin Cutan Med. Surg. (2008) 27(1):37-43.

Sarder, P., et al., "All-near-infrared multiphoton microscopy interrogates intact tissues at deeper imaging depths than conventional single- and two-photon near-infrared excitation microscopes," Journal of Biomedical Optics (2013) 18(10):106012-1-106012-11.

* cited by examiner

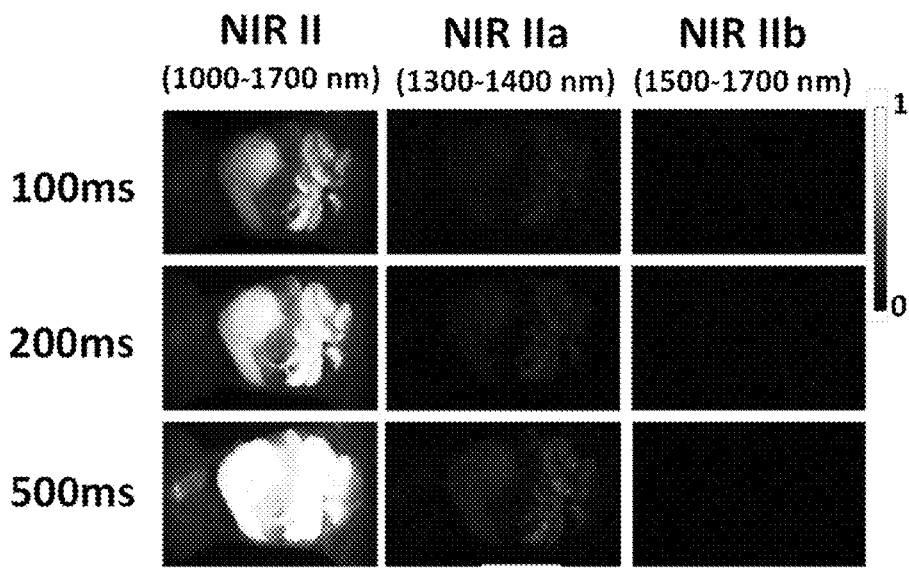
Fig. 6A
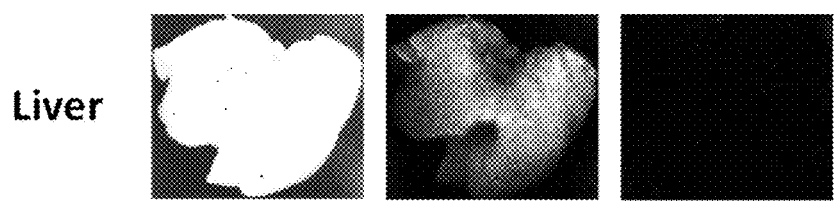
Fig. 6B
Figure 6A, 6B

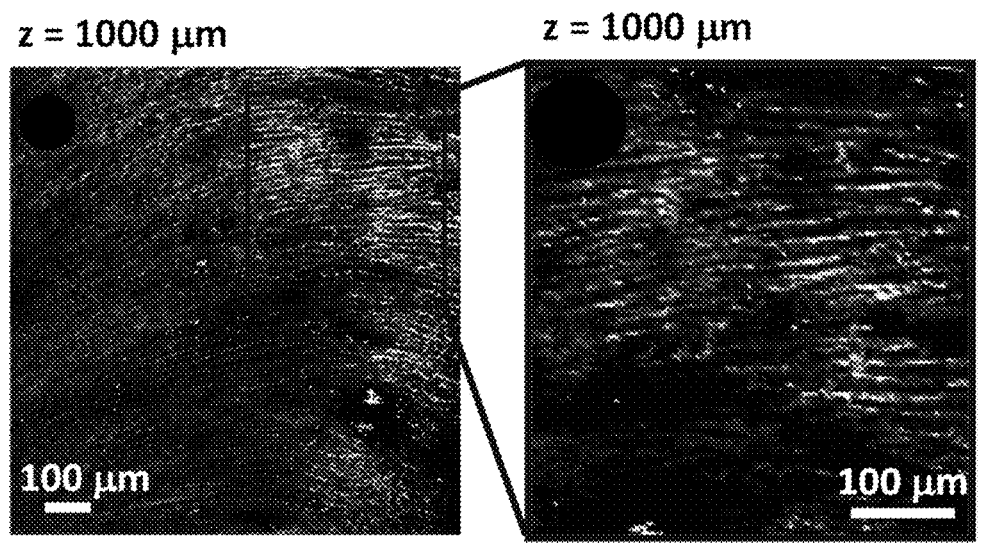
Figure 8A                    Figure 8B

NEAR-INFRARED-II CONFOCAL MICROSCOPE AND METHODS OF USE

CROSS-REFERENCE TO RELATED APPLICATIONS

This application claims priority from U.S. Provisional Patent Application No. 62/089,622, filed Dec. 9, 2014, which is hereby incorporated by reference in its entirety.

STATEMENT OF GOVERNMENTAL SUPPORT

This invention was made with Government support under contract 1137395 awarded by the National Science Foundation and under contract CA135109 awarded by the National Institutes of Health. The Government has certain rights in the invention.

REFERENCE TO SEQUENCE LISTING, COMPUTER PROGRAM, OR COMPACT DISK

None.

BACKGROUND OF THE INVENTION

Field of the Invention

The present invention relates to the field of near-infrared microscopy, and in particular, to confocal imaging for use in biological systems in the near-infrared range.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Fluorescence imaging in the second near-infrared window (NIR-II window, 1000-1700 nm) has attracted increasing interest in the past decade owing to the reduced scattering of photons inside biological tissues and thus elevated penetration depth for in vivo imaging, compared to traditional fluorescence imaging in the visible (400-750 nm) and short NIR (NIR-I, 750-900 nm) windows.[1-5] It has been found that the scattering of photons in a turbid biological medium scales inversely proportional with wavelength,[6] laying the foundation of deep tissue imaging with fluorescence photons in the long-wavelength NIR-II region. However, all previous reports on NIR-II imaging used widefield illumination to get snapshot images in two dimensions, limiting the NIR-II imaging method from reaching maximum depth of penetration, due to the existence of out-of-focus fluorescence when probing deeper optical slices.[5]

Specific Patents and Publications

Hong et al., "Near-Infrared II Fluorescence for Imaging Hindlimb Vessel Regeneration with Dynamic Tissue Perfusion Measurement," Circ Cardiovasc Imaging (Mar. 21, 2014) [Epub ahead of print], discloses development of NIR-II fluorescence imaging to image murine hindlimb vasculature and blood flow in an experimental model of peripheral arterial disease. An InGaAs camera was used.

Hong et al., "Multifunctional in vivo vascular imaging using near-infrared II fluorescence," Nat Med. 2012; 18:1841-1846, discloses in vivo real-time epifluorescence imaging of mouse hindlimb vasculatures in the second near-infrared region (NIR-II, 1.1-1.4 µm) is performed using single-walled carbon nanotubes (SWCNTs) as fluorophores. NIR fluorescence images were collected using a 1344×1024 pixel silicon CCD camera (Hamamatsu) for collecting photons in NIR-I and a liquid-nitrogen-cooled, 320×256 pixel two-dimensional InGaAs array (Princeton Instruments) for collecting photons in NIR-II.

Treado, et al., U.S. Pat. No. 6,734,962, "Near infrared chemical imaging microscope," discloses a near infrared radiation microscope. A multitude of spatially resolved spectra of transmitted, reflected, emitted or scattered near infrared wavelength radiation light from the illuminated area of the sample is collected and a collimated beam is produced therefrom. The microscope design uses NIR optimized liquid crystal (LC) imaging spectrometer technology for wavelength selection. The NIR optimized refractive microscope is used in conjunction with infinity-corrected objectives to form the NIR image on the detector with or without the use of a tube lens. An integrated parfocal analog color CCD detector provides real-time sample positioning and focusing.

Yi et al., US 20130230464, "Imaging Probe Including Nanoparticle," discloses an imaging probe that can include a photoluminescent carbon nanostructure configured to emit a wavelength of light detectable through living tissue. The device may use an imaging probe that is a carbon nanotube. For three-dimensional profile, a Xe lamp coupled to a monochromator was used as excitation source.

Sarder et al. "All-near-infrared multiphoton microscopy interrogates intact tissues at deeper imaging depths than conventional single- and two-photon near-infrared excitation microscopes," J. Biomedical Optics 18(10), 106012 (October 2013) discloses a comparison of three NIR excitation techniques: NIR single-photon confocal microscopy (NIR SPCM), NIR multiphoton excitation with visible detection (NIR/VIS MPM), and all-NIR multiphoton excitation with NIR detection (NIR/NIR MPM).

BRIEF SUMMARY OF THE INVENTION

The following brief summary is not intended to include all features and aspects of the present invention, nor does it imply that the invention must include all features and aspects discussed in this summary.

In general terms, the present invention comprises a method and device for fluorescence imaging in the near-infrared window, 800-1700 nm wavelength, and more particularly, in the second near-infrared window (NIR-II window, 1000-1700 nm), where tissue auto-fluorescence is minimized. The device enables improved imaging penetration depth and obtaining three-dimensional (3D) volumetric images based on optical sectioning. The device carries out to raster scanning and reconstructed 3D images of both ex vivo tissue samples and in vivo live animals. Images up to at least ~3 mm within tissue with a pixel resolution down to 3 µm can be achieved.

The present invention concerns the construction and intra-tissue imaging of a confocal microscope, including detecting fluorescence signals in a near-infrared (NIR) 800-1700 nm wavelength range, and surrounding NIR wavelengths, combining the deep penetration depth of NIR-II photons with the optical sectioning capability of confocal microscopy.

The present invention comprises, in certain aspects, a near-infrared (NIR) confocal imaging device, comprising: a light source, such as a laser; an optical structure defining an optical path from the light source to and through an objective lens, typically a series of mirrors, housings, filters, etc., said optical structure further comprising a beam splitter, such as a dichroic mirror, in the optical path, separating NIR excitation light from the light source from emission light from a sample; light from the objective lens is directed from there to a detector, such that light only returns to the detector when it is in focus; a translational stage which can be used during imaging in the x, y, and/or z direction, said translational stage being configured to support the sample and operative to cause movement relative to the objective lens during imaging. Typically, x and y would define a plane orthogonal to the impinging light beam, and z would define a depth into the plane and into or on the specimen. The movement of the translational stage is further synchronized with the detector, whereby the detector receives a series of light signals from a corresponding series of locations defined by the translational stage. The present confocal microscope further comprises a detector constructed for detecting light between about 800 nm to 1700 nm; and a logic device for synchronizing the translational stage with the detector, wherein the controlled stage is used for selecting image location relative to the sample, and the logic device further for data acquisition for storing and manipulating pixel data obtained from specific points defined by the x-y-z coordinates at a specific time during movement of the translational stage. A logic device may a comprise a programmed general purpose computer, a specialized computer with a central processing unit (cpu) designed specifically to carry out the instructions of movement, imaging, data processing, etc., as well as hard-wired logic devices. The logic device also produces a microscopic image for the user.

The source may itself produce NIR light and may comprise a laser, and will have sufficient energy to enter biological materials, e.g. skin. Energy may be output power as high as 1 mW.

In certain aspects and embodiments, the present invention comprises a device and method wherein the light source is one of (a) a red laser, emitting at a selective wavelength between 630 and 680 nm or (b) a near infrared laser emitting at a selective wavelength between 700 nm and 1350 nm, or (c) a far infrared laser emitting at a selected wavelength between 1350-1540 nm. In certain aspects and embodiments, the present invention comprises a device and method wherein the confocal microscope is comprised in a system comprising a sample on the translational stage. This includes a system in which the system comprises a fluorophore in the sample that is (a) an NIR fluorescent dye, (b) a quantum dot, (c) a carbon nanostructure, or (d) a carbon nanostructure that is an SWCNT linked to a biological affinity molecule, such as an antibody.

In certain aspects and embodiments, the present invention comprises a device and method wherein the optical structure comprises a first structure directing the light source to a dichroic filter directed through the objective lens, and a second structure for receiving light from said objective lens and said dichroic filter and directing light though a pinhole structure to the beam detector, said structures comprising light-exposed surfaces that do not absorb near-infrared light. Because the emission wavelength will be different from the excitation wavelength, the two beams can be separated, as described below.

In certain aspects and embodiments, the present invention comprises a device and method wherein the translational stage causes movement relative to a fixed-position objective lens, and the stage is moved during imaging in x and y directions to form a raster scan and at certain times in a z direction to define a focal plane for light directed to the detector. In certain aspects and embodiments, the present invention comprises a device and method wherein the translational stage comprises x-y motion control at a rate of approximately 1 MHz per scan. Z-movement may be at a slower frequency, and is synchronized with completion of an x-y scan.

In certain aspects and embodiments, the present invention comprises a device and method wherein the detector is an InGaAs avalanche photodiode (APD) or photo-multiplier tube (PMT) with near-IR sensitivity.

Further to the above-referenced methods, in certain embodiments the present invention comprises imaging a sample using an NIR confocal microscope, wherein the method comprises: optionally, combining the sample to be imaged with a near-infrared fluorescent label on portions of the sample; positioning the sample to be imaged on a translational stage and aligning the sample to receive light at a near-infrared excitation wavelength focused through a microscopic object lens; directing NIR light through an optical structure for (i) exciting the sample through NIR light directed through an object lens (ii) receiving emitted (emission) light through the object lens in a near-infrared wavelength, and (iii) directing received (emission) light to a near-infrared red detector, wherein said detector is operatively connected to a logic device, wherein said optical structure does not move internally during said exciting, receiving, and directing steps; moving said translational stage in an x-y direction under control of said logic device to obtain a raster scan of the sample; either moving said translational stage in a z direction and synchronizing z direction movement with receiving light while moving in an x-y direction, or holding said translational stage at a fixed z position; and constructing light data, using said logic device, to obtain an image of the sample.

In certain aspects and embodiments, the present invention comprises a method wherein the imaging is of a cell, a tissue sample, or an ex vivo tumor sample. In certain aspects and embodiments, the present invention comprises a method wherein the light source is constructed as described above and/or the near infrared fluorescent label is added to the sample, as described above.

In certain aspects and embodiments, the present invention comprises a method wherein a translational stage moves in the x, y and z directions and a slice-by-slice image is produced. In certain aspects and embodiments, the present invention comprises a method wherein the images are at least one 1 mm below the surface of the sample. In certain aspects and embodiments, the present invention comprises a method wherein a slice-by-slice image is constructed into a three dimensional image. Using a predefined, set z dimension (depth, or distance from the objective lens), the x and y directions are scanned in a raster pattern to allow assembly of a pixel-by-pixel two dimensional image at a set z depth into the sample. Furthermore, using a selection of pixels from a range of either x or y dimension, and a selection of pixels from a series of z depths, a logic device (e.g. a programmed computer) can assemble the pixels into an image orthogonal to the direction of the excitation/emitted light. Using these techniques, one may obtain an NIR image or series of images (perspective view) representing a defined volume of a sample, e.g. between 30 μm×30 μm×30 μm and 600 μm×600 μm×240 μm volume containing selected 2D slices.

In certain aspects and embodiments, the present invention comprises a method wherein the translational stage is moved at a frequency of 0.5 to 1 MHz in the x, y and z directions. The inventive method may employ a near-infrared detector that detects infrared at a wavelength between about 800 nm to 1700 nm. Alternatively, the near-infrared detector detects infrared at a wavelength between about 1300 nm to 1700 nm.

In certain aspects and embodiments, the present invention comprises a method wherein the near-infrared detector is an InGaAs detector, including an InGaAs avalanche photodiode (APD); or the NIR detector is a photo-multiplier tube (PMT) having near-IR sensitivity. The photodiode may be provided as an array to receive different beams.

In certain aspects and embodiments, the present methods and devices comprise preparation of an image that has been obtained from a depth of at least 3 mm in a biological tissue. The biological tissue may be one such as exemplified here, e.g. mammalian organs such as brain or lymph node, or a tumor, or other tissues. The image may be a slice at a predetermined depth, i.e. in an x-y direction, or may be a computed image viewed along the z direction.

In certain aspects, the present invention comprises methods such as described above, such as imaging a biological sample using a confocal microscope, comprising steps of (a) contacting the biological sample with near-infrared from a near-infrared light source; scanning the light (e.g. raster scanning) relative to the sample to construct an image at a defined depth, where such scanning may be carried out by the translational stage as described above; (b) detecting light emitted from the sample from the near-infrared light source, using a detector detecting light in a wavelength of between 1500 nm and 1700 nm, wherein (c) said detecting comprises the use of a single point light detector, and said method further comprising one of: imaging of molecules treated in a immunohistochemistry staining or FISH (fluorescence in situ hybridization) protocol, imaging of a single cell, imaging of a tissue, imaging of a labeled protein (including on antibody protein), nucleic acid imaging, and microarray imaging. A single point light detector may be an Indium Gallium Arsenide (InGaAs) or Germanium (Ge) single point detector, and is to be contrasted with a planar array detector, e.g. a camera.

BRIEF DESCRIPTION OF THE DRAWINGS

FIG. 6A, 6B shows a series of autofluorescence images from a mouse body (6A) and ex-vivo liver sample (6B) in various subregions upon different exposure times from 0.1 s to 0.5 s. It shows that the NIR-IIb region (1500-1700 nm) exhibits almost zero autofluorescence for all major organs and tissues up to an exposure time of 0.5 s, which is much longer than most of the imaging exposure times required for NIR fluorescence imaging.

FIG. 8A, 8B is a pair of confocal images of cardiac microvessels.

DETAILED DESCRIPTION OF THE PREFERRED EMBODIMENT

Overview

Figure 1A:
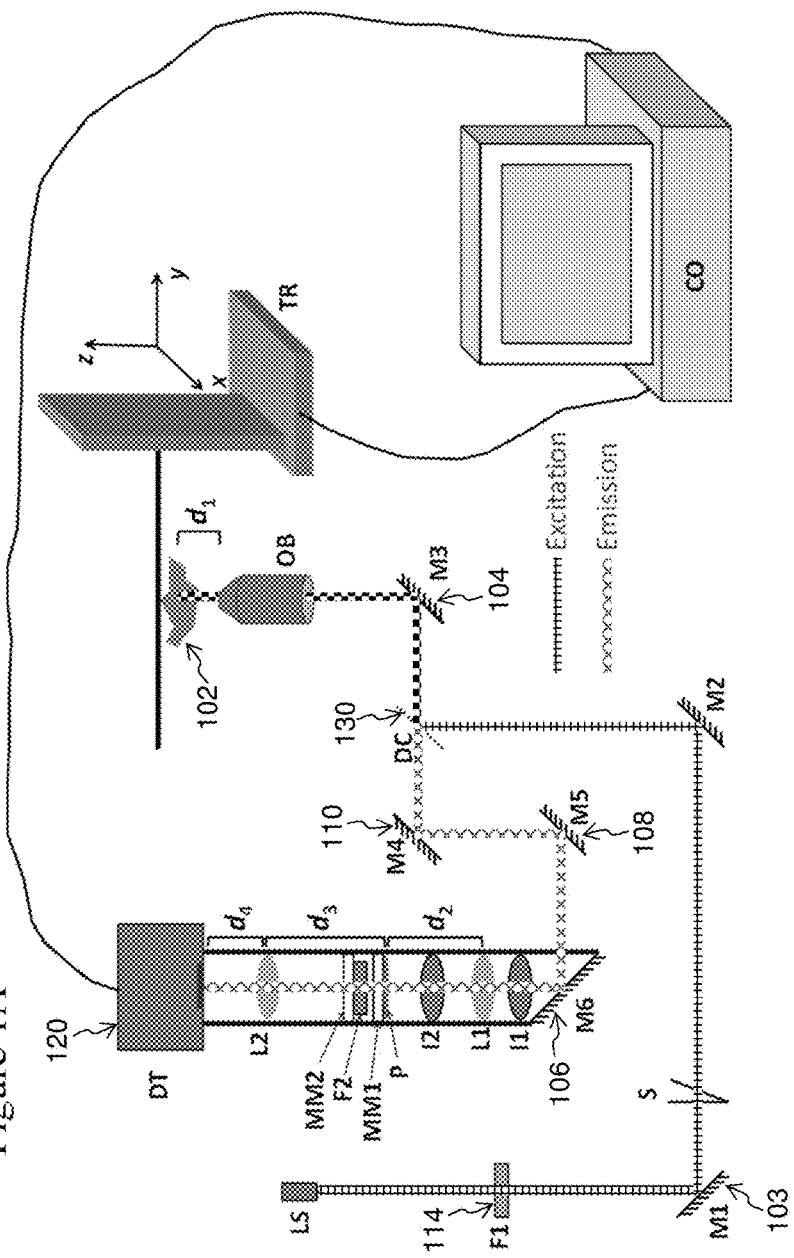
FIG. 1A is a schematic illustration of an NIR-II confocal microscope setup according to the present invention, including the translational stage and computer control and image construction.

The present NIR confocal microscope is capable of detecting fluorescence signals in the near-infrared (NIR) 800-1700 nm wavelength range using a variety of NIR-I (800-1000 nm) and NIR-II (1000-1700 nm) dyes and nanomaterials. The NIR-II window, in comparison with shorter-wavelength optical windows such as the visible (400-750 nm) and the traditional NIR (NIR-I, 750-900 nm) regions, has the benefits of significantly reduced photon scattering owing to the inversely proportional relationship of scattering versus wavelength, and thus allows for in vivo fluorescence imaging with much deeper penetration and crisper feature widths. The present NIR confocal microscope can be used on samples labeled with NIR-II fluorescent materials including single-walled carbon nanotubes (SWCNTs), semiconducting quantum dots and conjugated copolymers to further enhance image resolution.

The present NIR confocal microscope has particular application to in vivo imaging, due to the high resolution and depth of the device in the NIR region. The present confocal microscope uses particular materials designed for transmitting and receiving emissions in the NIR range, such as the laser light source, a structure defining an optical path (reflective and transmissive surfaces), NIR fluorescent labels, and detectors that operate in the NIR range.

The term "optical path" refers to the various components that impinge upon and/or alter the light either emitted or detected in the present microscope. By way of the example in FIG. 1A, this includes the light passing from the NIR laser, the various filters, mirrors (including dichroic mirror or other beam splitter), pinhole structure, objective lens and detector. The optical path, as described here, need not be moved during operation in order to create the various images obtained at various slices within the sample, or to construct slices in a defined x-y point to construct an orthogonal image (computerized tomography). The optical path is constructed and designed to be used with NIR. That is, the various surfaces are used for, and may be optimized for, such wave lengths, without undesirable loss of radiation due to scattering, absorption, etc.

A variety of beam splitters are commercially available. Plate beamsplitters have a coated front surface that determines the beam splitting ratio while the back surface is wedged and anti-reflective coated in order to minimize ghosting and interference effects. Pellicle beamsplitters provide excellent wavefront transmission properties while eliminating beam offset and ghosting. Cube beamsplitters are available in polarizing or non-polarizing models. The pellicle and cube beamsplitters can be purchased pre-mounted in cubes that are compatible with the present lens tube and cage systems. Dichroic beamsplitters exhibit beam-splitting properties that are wavelength dependent. They are useful for combining/splitting laser beams of different color.

Ranges: For conciseness, any range set forth is intended to include any sub-range within the stated range, unless otherwise stated. As a non-limiting example, a range of 1000 to 1700 is intended to include a range of 1200-1210, 1200-1300, 1500-1600, 1650-1710 etc. The term "about" has its ordinary meaning of approximately and may be determined in context by experimental variability. In case of doubt, the term "about" means plus or minus 5% of a stated numerical value.

The term "NIR" or "NIR range" means near infra-red light, particularly in the sense of NIR fluorescence. The term also refers specifically to the near infra-red region of the electromagnetic spectrum (from 0.75 to 3 μm). The term NIR-II means near infrared of a wavelength between about 1000 nm and 1700 nm. For purposes of biological imaging, the NIR range is divided into NIR-I, around 800-1000 nm and NIR-II, between about 1000 and 1700 nm. The NIR-IIb region is between about 1500-1700 nm. As shown below, the NIR-IIB region can produce more clear images in the present method and device.

The term "fluorophore" is used herein in a general sense to refer to a fluorescent molecule that can re-emit light upon light excitation. It can include molecules commonly used in fluorescence imaging such as fluorescein isothiocyanate (FITC), rhodamine, coumarin, cyanine, and their derivatives. It can include single-walled carbon nanotubes (SWCNTs), semiconducting quantum dots (QDs), conjugated polymers and small organic molecule fluorophores. It can include proteins or peptides such as elastin, collagen, and phenylalanine. "NIR-II fluorophore" means a fluorophore with an emission spectrum falling within the entire NIR region of between about 800 and 1700 nm. In the present methods, NIR-II fluorphores are useful in the use of the present confocal microscope. They may be contained in biological samples such as cells, organs or whole bodies.

Although some of the biological samples imaged here will auto-fluoresce at different wavelengths, often auto-fluorescence is to be avoided by choosing an appropriate NIR wavelength. A variety of NIR fluorophores and labels can be used to enhance imaging. These include dyes and nanotubes such as SWCNTs. The term "SWCNT" means single-walled carbon nanotube. A carbon nanotube is a tube that contains a sheet of graphene rolled into a cylinder as small as 1 nm in diameter. Carbon nanotubes may include other materials. Carbon nanotubes, as used herein, include structures that are not entirely carbon, such as BCN nanotubes. The present carbon nanotubes may also be graphene in other forms.

The present confocal microscope may use a relatively low cost InGaAs (Indium Gallium Arsenide) avalanche photo-diode (APD) or photo-multiplier tube (PMT), or other NIR sensitive photodiode detectors, and does not rely on expensive 2D InGaAs cameras.

The present methods include use of the NIR confocal microscope above for imaging biological samples with low autofluorescence in the 800-1700 nm region. In particular, zero-autofluorescence imaging is achieved in the so called NIR-IIb 1500-1700 nm range. Even the most auto-fluorescent liver tissues are found to give no auto-fluorescence in the NIR-IIb imaging window, allowing single molecule fluorescence imaging in any biological sample.

The present methods include using the NIR confocal microscope above for immunohistochemical (IHC) staining and FISH (fluorescence in situ hybridization) assays. Protein biomarkers and nucleic acids (DNA, RNA, etc.) are detected by NIR-II imaging with ultra-low background and high sensitivity. NIR-IHC and NIR-FISH can also be combined with conventional color based staining methods.

The present devices and methods use an X-Y-Z translational stage that can rapidly and accurately change the relative position of the sample in reference to the objective lens and the light. The term "translational stage" is used herein to refer to an apparatus used to precisely position and/or move an object. A linear translation stage is used to precisely position and/or move an object along a single axis of horizontal linear travel. Linear translation stages may include a moving platform and stationary base joined by a bearing system. Position may be controlled with a precision linear actuator like an adjustment screw, micrometer head, or motorized actuator. A "3D translation stage" means a translation stage for precisely positioning and/or moving an object along three axes, typically orthogonal (x, y, and z). It may comprise three linear translation stages assembled for multi-axis travel. Using this translation stage, the present methods and devices can use mirrors and filters that do not need to be moved during acquisition of an image.

As is described below, the translational stage is moved in specified ways to travel across an x and y direction, creating a "raster scan," i.e. creating an image whereby light pixels are beamed (scanned) onto the light detector a line at a time from (e.g.) left to right starting at the top-left corner. At the end of the line, the beam is turned off and moved back to the left and down one line, which is known as the "horizontal retrace." When the bottom-right corner is reached, the light source is returned to the top-left corner, known as the "vertical retrace." For TV signals, by analogy, these "flyback" periods in which the electron beam is moved to a different line are also called the "horizontal" and "vertical blanking intervals." As is known in other imaging techniques, the raster scan may be carried out in an x-y plane, and carried out at various z (depth) positions, creating a thin slice image that can be manipulated by computer tomographic methods to generate three dimensional images of the sample. This slice imaging is further described, e.g. in U.S. Pat. No. 4,149,247, "Tomographic apparatus and method for reconstructing planar slices from non-absorbed and non-scattered radiation." As noted, the present scan may be created by movement of the translational stage in a variety of x-y-z directions, including a rotational movement.

The three dimensional stage comprises actuators that can move the sample surface through directions generally referred to as x and y (orthogonal and parallel to the plane of the paper) and orthogonal to the plane of the paper, i.e. "in" to the paper. The actuators are computer controlled and carry out high resolution, very fine movements.

The present methods and devices can create an image in the NIR region of a microscopically enlarged image (e.g. up to 100-1000x) using a single point detector that can detect low NIR light intensity. The image is synthesized by a series of pixels. These detectors may be, as one example, avalanche photodiodes. These avalanche photodiodes (APDs) are silicon photodiodes with an internal gain mechanism. As with a conventional photodiode, absorption of incident photons creates electron-hole pairs. A high reverse bias voltage creates a strong internal electric field, which accelerates the electrons through the silicon crystal lattice and produces secondary electrons by impact ionization. The resulting electron avalanche can produce gain factors up to several hundred.

Si APDs can be used when light signals are too high for photomultiplier tubes and too low for conventional photodiodes. Si APDs are often used in high-speed applications since the excess noise from the avalanche process is still lower than the noise that would be generated in connecting an external amplifier to a conventional photodiode operated at high frequencies. Typical applications include low-light level measurement, spectroscopy, range finding and spatial/fiber optic communication. Both short-wavelength type and near infrared detection types are hermetically sealed in a metal package with a clear glass window.

Alternatively, an NIR-photmultiplier tube may be used for detection in the desired wavelength. NIR-PMTs (near-infrared photomultiplier tubes) are photodetectors that provide high-speed response and high sensitivity in the near infrared region. These are ideal for detecting high-speed phenomena occurring at low light levels such as in measurements of photoluminescence, fluorescence lifetime, Raman spectroscopy, cathode luminescence, and singlet-oxygen emissions. Such products are made by Hamamatsu Photonics. Photomultiplier tubes are described e.g. in U.S. Pat. No. 4,853,595, "Photomultiplier tube having a transmission strip line photocathode and system for use therewith."

The term "fixed" in connection with a component in the present near infrared confocal microscope means that the fixed component is attached to and/or mounted in the microscope in a fixed position during use, as opposed to confocal microscope component that rely on rotating or spinning structures.

General Method and Device Construction

This setup is believed to represent the first confocal microscope in the world for transmission and fluorescence imaging in the NIR-II window (800-1700 nm). All previous reports on microscopic NIR-II imaging (or SWIR imaging, short-wavelength infrared imaging[4]) used widefield illumination to get snapshot images in two dimensions using expensive 2D InGaAs cameras.[1,10-16] Here, the NIR confocal microscope can use a much lower cost single-pixel InGaAs APD or PMT, making it much more affordable and feasible to perform NIR-II imaging.

The confocal NIR-II microscope allows the user to acquire depth-solved images with higher spatial resolution (approaching the diffraction limit) and less background interference. With the deep penetration depth of NIR-II fluorescence inside turbid biological tissues, and the exclusion of out-of-focus background from the confocal setup, an imaging depth of up to 3 mm has been achieved inside biological tissue samples, which has never been achieved before by regular widefield NIR-II microscopy. The expected maximum depth of imaging could be up to 1 cm with the optimal NIR-II fluorophores.

The present imaging method using the NIR-confocal microscope can be used for slice by slice 3D imaging of biological tissues throughout a thickness up to 5 mm in the NIR-II window. The reduced scattering in NIR-II allows for tissue penetration up to 5-10 mm, superior to ~0.2 mm afforded by conventional imaging.

The confocal NIR-II microscope depicted in FIG. 1A, with part abbreviations given in Table 1, represents the first raster-scanning confocal microscope that does not use any scanning mirror, which is widely used in all traditional confocal microscopes.[17,18] The confocal NIR-II microscope uses a fast-moving 3D translation stage with constant moving velocity, eliminating any image distortion induced by a non-linear resonant galvanometer and the need for phase correction based on pixel clock. In addition, the instrument can also use conventional galvo mirrors for scanning.

A key to the microscope is the use of a variety of NIR-I (800-1000 nm) and NIR-II (1000-1700 nm) materials, and, if used with dyes, NIR dyes. Also, the confocal microscope uses a relatively low cost InGaAs avalanche photodiode (APD) or photo-multiplier tube (PMT), and does not rely on expensive 2D InGaAs cameras. The basic setup has the components listed in Table 1 below (with other possible variations):

TABLE 1

A list of components in the NIR-II confocal microscope setup.

| Part Abbreviation | Full Name | Company | Catalog number |
|---|---|---|---|
| CO | Computer, with visual display | / | / |
| DC | Dichroic filter, 850 nm | Edmund Optics | #69-895 |
| DT | detector | / | / |
| F1 | Filter, 750 shortpass | Omega Filters | 3RD750SP |
| F2 | Filter, 1000 longpass | Thorlabs | FEL1000 |
| I1-I2 | Iris diaphragms on SM1 threaded cage plate | Thorlabs | SM1D12D, CP02T |
| L1 | 200 mm lens on a z-axis translation mount | Thorlabs | AC254-200-C, SM1Z |
| L2 | 30 mm lens in a fixed lens tube | Thorlabs | AC254-030-C, SM1L05 |
| LS | Laser | Thorlabs | HL6545MG |
| M1-M5 | Mirrors | Thorlabs | PF10-03-P01 |
| M6 | Mirror on a cage mirror mount | Thorlabs | PF 10-03-P01, KCB1 |
| MM1-MM2 | Magnetic mounts for cage system | Thorlabs | CP90F |
| OB | Objective, 100x | Olympus | ULWD MS Plan 100 IR |

TABLE 1-continued

A list of components in the NIR-II confocal microscope setup.

| Part Abbreviation | Full Name | Company | Catalog number |
|---|---|---|---|
| P | Pinhole, 150 μm | Thorlabs | P150S |
| S | Manual shutter | Thorlabs | LB1, FM90 |
| TR | 3D translation stage | Newport | VP-25XA-XYZR |

Referring now to FIG. 1A, the optical path begins with laser excitation. The light passes through a filter 114 for selecting a specific desired NIR wavelength. The optical path is directed by mirrors, arranged for convenience, to a dichroic mirror 130, which separates the path of the excitation light from the emission light from the sample. The light goes from there to another mirror and then through the objective lens and to and into the sample 102. Light emitted from the sample 102 goes from there back through the objective lens and the dichroic mirror 130, from there to mirrors 110, 108, 106, and then to a lens for focusing the light thought pinhole, a second filter, a second lens, and then finally to the detector 120. As described below, the sample is mounted on a 3D translational stage that is synchronized with the detector 120. The detector 120 transmit detect light to a computer CO, that creates a user-selected image of the sample.

Key components in the NIR-II confocal setup include the following, which distinguish this novel confocal setup from previous confocal designs:

The detector (DT): a wide selection of detectors with sufficient sensitivity in the 800-1700 nm NIR region can be used in this confocal setup. This includes, without limitation, an indium-gallium-arsenide (InGaAs) photodiode, InGaAs avalanche photodiode (APD), InGaAs photomultiplier tube (PMT), InGaAs 1D detector array, and InGaAs 2D detector array. This wide selection of NIR-sensitive detectors allows one to take 2D and even 3D NIR images without the necessity of using an array detector made of InGaAs, which is usually much more expensive and bandwidth-limited.

The three dimensional (3D) translation stage (TR): The translation stage that can move at a constant, fast velocity allows the user to perform a raster scan without using a galvanometer mirror, using careful synchronization between the 3D translation stage and the detector enabled by the LabVIEW user interface. The confocal setup can perform data acquisition at a rate of up to MHz, and complete each 2D scan within seconds. The exemplified translational stage can be provided with a standard encoder output with 0.1 μm resolution, that is compatible with other motion controllers. The device also provides a 1 Vpp analog encoder interface compatible with a motion controller. These stages deliver a reliable 10 nm motion sensitivity, and better than 140 nm bi-directional repeatability.

The present 3D translational stage replaces the need for resonant and galvanometric mirrors to scan the laser beam. Instead, the motion of the sample stage is programmed to achieve a 3D raster scan in the stage-scanning mode while keeping the excitation laser beam stationary. This stage-scanning method avoids the need for pixel clock correction for resonant mirrors, which is intended to correct for the non-linearity of the resonant scanner velocity. In our stage-scanning implementation of the NIR-II confocal microscope, the stage is programmed to perform linear translational motion at a fixed, constant velocity for each fast axis scan, which is synchronized with the continuous image capture of the 2D InGaAs array and set with a moving velocity that is given in the following equation, $$v(\text{linear stage}) = \frac{\Delta x}{\Delta t} = \frac{\Delta x}{t_{exp} + t_{overhead}}$$

where $\Delta x$ is the desired pixel resolution and $\Delta t$ is the average time the 2D InGaAs camera stays for acquiring the intensity for each pixel, which is the sum of the exposure time for each pixel and the intrinsic overhead time of the acquisition (1.7 ms for the 2D OMA V camera).

The NIR-II fluorophores: a variety of NIR-II fluorophores with different emission wavelengths and fluorescence quantum efficiencies can be used for the NIR-II confocal imaging. This includes, without limitation, single-walled carbon nanotubes (SWCNTs),[3] semiconducting quantum dots (QDs),[7] conjugated polymers and small organic molecule fluorophores.[8] The emission spectra of the aforementioned fluorophores would cover the entire NIR region from 800 nm to 1700 nm, allowing one to select the optimum fluorophore(s) that fits the individual need.

As illustrated in FIG. 1A, a sample is located at a 3D translation stage TR. A detector DT (120) detects NIR fluorescence emitted from the sample. A computer CO, operably connected to TR and DT 120, synchronizes TR and DT for confocal scanning and data acquisition. A laser source LS generates a 660 nm laser beam that passes through a 750 nm shortpass filter F1 (114) that cleans the laser line. The beam is reflected by mirror M1(103) and passes through manual shutter S, which is a beam block mounted on a flip mount. The beam is subsequently reflected by mirror M2, 850 nm dichroic filter DC (130) and mirror M3 (104) before passing through objective OB and reaching the sample on the 3D translation stage TR. NIR fluorescence emitted from the sample passes in the opposite direction through the objective OB, is reflected by mirror M3 (104), and passes through 850 nm dichroic filter DC (130). It is directed into a cage system after reflecting off of mirrors M4, M5 and M6 (110, 108, 106). M6 is on a cage mirror mount. Mirrors M1-M6 are protected silver mirrors with a broad reflection band covering the NIR-II. In the cage, the detectable fluorescence first passes through iris diaphragm I1, lens L1, and iris diaphragm I2. Iris diaphragms I1 and I2 aid in alignment in the cage. The fluorescence then passes through 150 μm pinhole P, 1000 nm longpass filter F2, and lens L2. The size of the pinhole is determined by Airy disk size×magnification. Lenses L1 and L2 have an anti-reflection coating in the 1050-1620 nm range. Magnetic mounts MM1 and MM2 secure P and F2, respectively, to the cage. Finally, the fluorescence reaches and is detected by detector DT (120), which can be a single-chip photodiode, APD, PMT or 1D and 2D InGaAs arrays with sufficient sensitivity in the NIR-II (1000-1700 nm). Certain examples here use a 320×256 pixel 2D InGaAs array (2D OMA V, Princeton Instruments) as the photodetector, which allows performance of both confocal and wide-field fluorescence imaging using the same detector. It is noteworthy that when the 2D InGaAs array was used in the confocal mode, since the confocal microscope obtained the images by acquiring the data pixel by pixel, only 4 pixels from the entire array of 320×256 pixels were used and binned into one single intensity value for each pixel.

In the present embodiment, all components in front of the detector (M6 to L2) are mounted inside a cage system. The distances $d_1$ to $d_4$ are critical to the alignment of this setup.

Figure 1B:
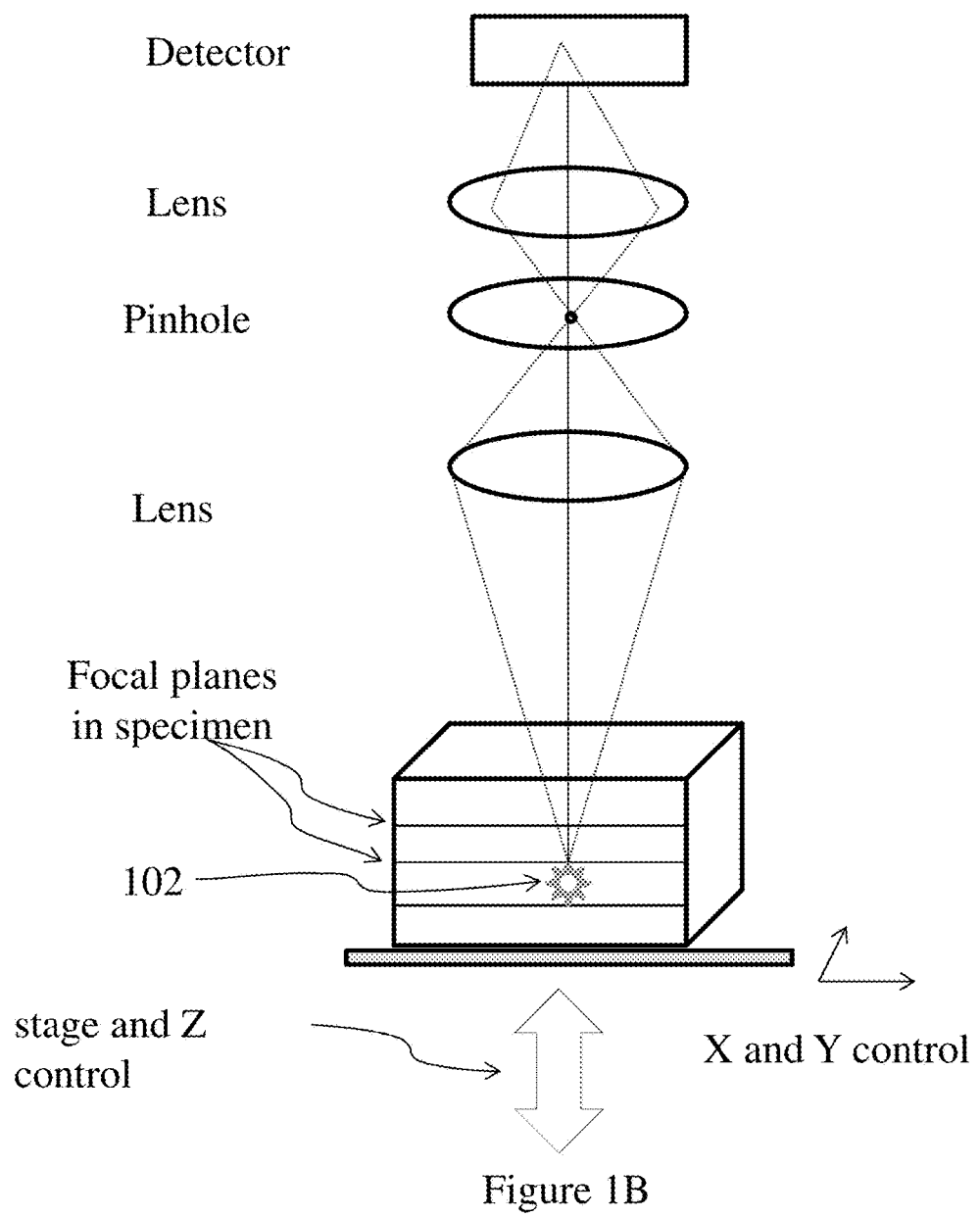
FIG. 1B is a schematic illustration of the arrangement of the present NIR detector and "3D" (three dimensional, or so-called X-Y-Z) translational stage, showing synchronization of a focused beam applied to focal planes in a specimen with the X-Y-Z movement of the stage to obtain images by data acquisition. As can be seen by the point source 102 in FIG. 1B, at a specific X, Y, Z coordinate within the specimen, a three dimensional, or tomographic image can be constructed. The sequential passage of the light emitted from a point in a specific focal plane of the specimen passes to the detector through a lens, pinhole and second lens, as shown. The emission light path is stationary, but the stage moves in the X, Y and Z directions so that optical sections from different focal planes may be obtained. Data acquisition is synchronized so that it occurs when the stage moves along the X-axis alone.

FIG. 1B illustrates a basic arrangement for obtaining optical serial sections without moving a lens or mirror, but, rather moving the stage on which the sample sits. This is in contrast to a traditional confocal microscope, which scans the sample by spatially modulating the excitation beam through the lens (usually through a galvo mirror), and which requires de-scanning the emission through the same galvo mirror. In the present device, the excitation beam and the emission path remain stationary during imaging. Part of this arrangement relies on a series of logic steps programmed into the computer. Via the detector, the computer acquires image data in synchrony with the motion of the stage. The computer instructs the stage to move at a high, constant velocity along the X-axis beginning from a specified starting site. Data of single points of emitted light are acquired at evenly spaced intervals along the path. Once the linear scan along the X-axis is complete, data acquisition is paused as the computer instructs the stage to reposition itself, by motion along the X- and Y-axes, at another starting site to begin a subsequent X-axis scan. The stage again moves along the X-axis to acquire data in an identical manner. The process of repositioning and scanning is repeated multiple times, the resulting movement of the stage being in a raster pattern, until data sufficient to generate a desired optical section is obtained. After completing acquisition of data for the optical section, the computer instructs the stage to reposition itself to a different focal plane by moving along the Z-axis, so that data may be acquired to generate another optical section, in a manner identical to that for the previous optical section. Optical serial sections may be obtained in this way.

In summary, in the present scanning stage confocal microscope, both the excitation beam and the emission path remain stationary, avoiding the need for de-scanning the emission fluorescence path. To achieve scanning, the stage moves at a high, constant velocity along the fast axis X-axis (matching the velocity of the excitation beam steering in traditional confocals), and the stage sweeping motion is also synchronized with the camera data acquisition. Since the motion of the stage is linear, the pixels along the fast axis are evenly spaced. In contrast, for a scanning beam confocal, since the angular motion is linear, the pixels become denser at two ends while more sparse in the center; also, pixel clock correction is needed for the pixel clock problem in traditional confocal microscopes. In contrast to a traditional scanning beam confocal microscope, the present scanning stage confocal microscope does not require de-scanning of the emission path and does not require pixel clock correction. In a traditional confocal microscope, the synchronization is carried out between the scanning mirror (that steers the excitation beam) and the detector. In the present confocal microscope, synchronization is between the sample stage and the detector.

The present system, as exemplified, is customizable in a variety of ways. For example, a 660-nm laser is used below, but lasers with other wavelengths can be used too. As another example, a 100× objective is used below, but depending on the desired resolution and scanned area, objectives with other magnifications can be used. As another example, the 1000 nm longpass filter F2 is for collecting fluorescence in the 1000-nm long region, but can be replaced with filters for different NIR subregions.

EXAMPLES

Example 1: Basic Operation Procedure

The setup is assembled according to FIG. 1A. The excitation laser beam should hit the center of F1, M1, S, M2, DC and M3.

The excitation beam is aligned to be perfectly vertical after bouncing off from M3. This is done with an additional iris diaphragm connected to lens tubes with different lengths. The iris diaphragm is moved along the vertical axis while adjusting the angles of DC and M3 to walk the beam and confirm that the excitation beam always hits the center of the iris.

For aligning the reflected light, a highly reflective sample with NIR-II fluorophores is used. Such a sample can be made by spin-coating water-soluble, surfactant-stabilized single-walled carbon nanotubes (SWCNTs) onto a thick gold coated glass substrate, according to our previous publication.[9] The height of this sample is adjusted via TR while watching for the reflected laser beam between DC and M4. Fine adjustment of TR is made to reach the smallest beam size.

The reflected excitation beam is relayed from M4 to M6 by making adjustments to ensure that the beam hits roughly the center of each mirror.

The reflected beam is walked by adjustments to the angles of M5 and M6. The reflected beam should always hit the center of I1 as it moves along the rail of the cage system.

The diaphragm of I1 is opened all the way and L1 is moved as close as possible to I1. Watching for the focused excitation beam after L1, fine beam walking is performed by adjusting the angles of M5 and M6 and making sure the focused beam always hits the center of I2 as it moves along the rail of the cage system.

F2 is attached to MM2 while MM1 is left unloaded. I2, with a closed diaphragm, is moved as close to MM1 as possible to mimic a pinhole (I2 with closed diaphragm would make a pinhole of ~500 μm). It must be ensured that distances $d_2$ and $d_1$ satisfy the following relationship:

$$\frac{d_2}{d_1} = \frac{f_{L_1}}{f_{OB}}$$

where $f_{L_1}$ and $f_{OB}$ are the focal lengths of L1 and OB, respectively.

L2 and DT are placed with respect to MM1 such that distances $d_3$ and $d_4$ satisfy the following relationship:

$$\frac{1}{d_3} + \frac{1}{d_4} = \frac{1}{f_{L_2}}$$

where $f_{L_2}$ is the focal length of L2.

The signal on the detector (read out from the computer) is maximized by fine adjustment of the angles of mirrors M5 and M6 as well as the position of L1 on the rail of the cage system. The diaphragm of I2 is opened and closed to ensure that the center of the diaphragm is concentric with the laser spot illumination in the image of the sample.

P is attached to MM1 and then the diaphragm of I2 is opened all the way. The pinhole size of P is given by the following formula:

$$\text{pinhole size} = \frac{1.22\, \lambda}{NA} \times M$$

where λ is the wavelength of the detected fluorescence, NA is the numerical aperture of the objective and M is the magnification of the objective given that the right tube lens (L1) with the same focal length as specified by the manufacturer of that specific objective is used.

If the fluorescence emission has been well aligned during the previous step of maximizing the signal, the DT should still pick up sufficient signal from the sample, showing up as a tiny bright dot on the computer monitor.

The highly reflective, standard sample is replaced with a real sample for confocal imaging. M5, M6 and L1 are adjusted to reach maximum intensity of the signal. For easy alignment, TR can be moved to find a bright spot in the sample. If a bright spot in the sample remains difficult to find in the confocal mode, it is recommended that two collimating lenses be placed between LS and F1, one offset lens be placed between M2 and DC, and the pinhole P be detached from MM1 to perform widefield microscopic imaging.

When signal in the confocal mode is optimized, confocal scanning is started. The stage TR will start raster scanning at a high speed while the detector will be collecting signals in a continuous manner.

Example 2: Confocal Images

Figure 2:
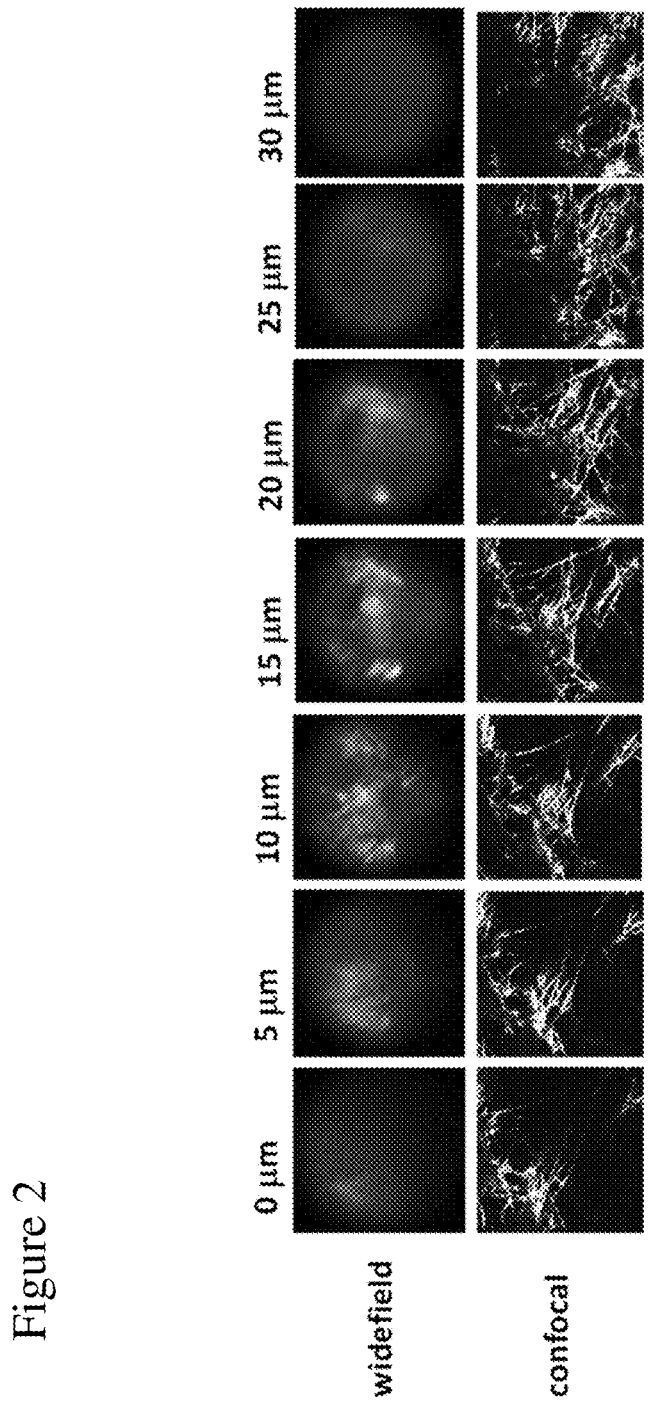
FIG. 2 is a series of photographs showing a side-by-side comparison between widefield fluorescence images and confocal fluorescence images in the NIR-II window for the same sample, focused at different depths.
Figures 3A, 3B, 3C, 3D:
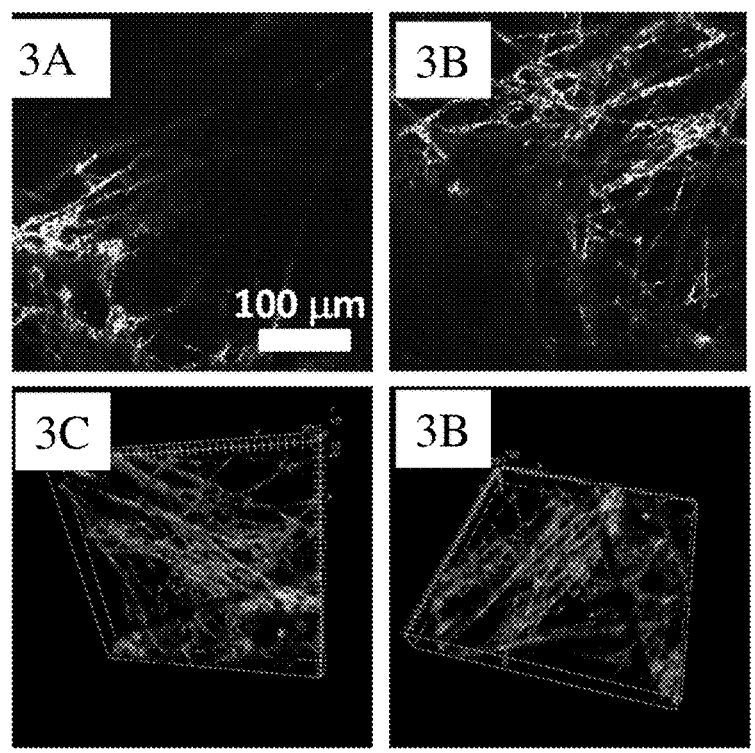
FIG. 3A-3D shows confocal fluorescence images of gold-coated glass fibers adsorbed with NIR-II fluorescent SWCNTs. 3A&B are typical NIR-II confocal fluorescence images of the sample at two different depths. 3C&D are 3D reconstructed images of the sample, showing perspective views of the fiber network. This shows that various images can be constructed including top, bottom and side views, to at least 100 μm depth.
Figures 4A, 4B, 4C, 4D, 4E, 4F, 4G, 4H, 4I:
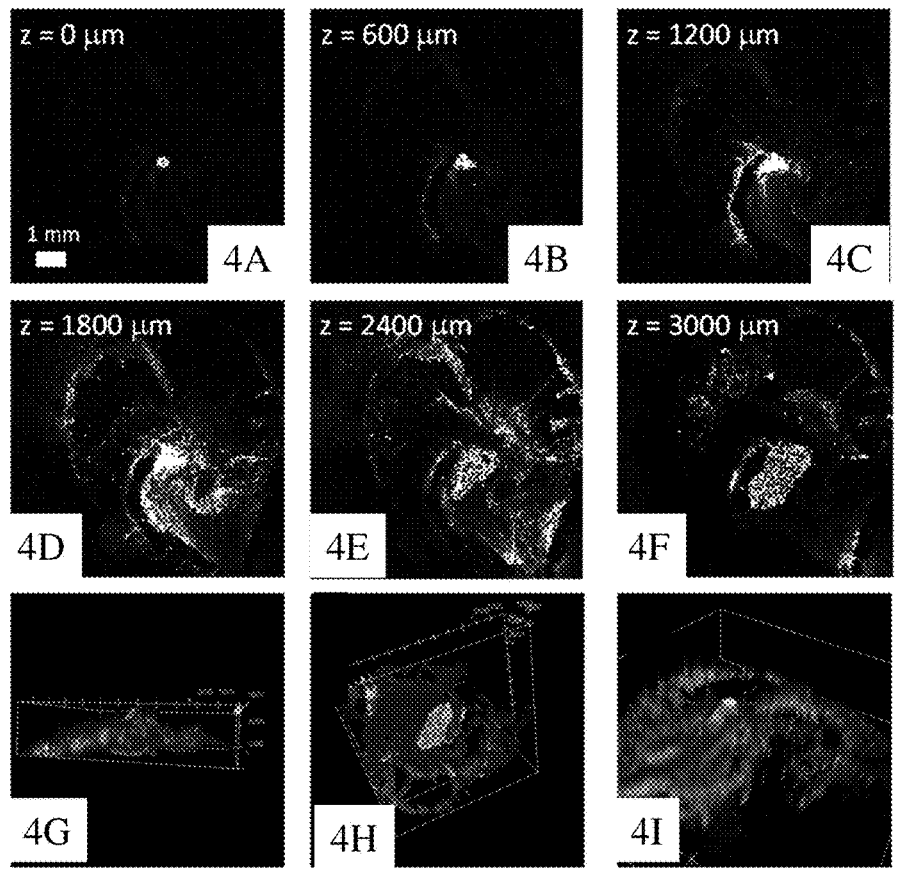
FIG. 4A-4I shows confocal fluorescence images of an ex vivo tumor sample injected with NIR-II fluorescent SWCNTs. 4A-F are typical NIR-II confocal fluorescence images of the tumor at different depths ranging from 0 mm to 3 mm. 4G-I are 3D reconstructed images of the tumor sample, showing perspective views of the distribution of SWCNTs inside the tumor body.
Figures 5A, 5B, 5C, 5D:
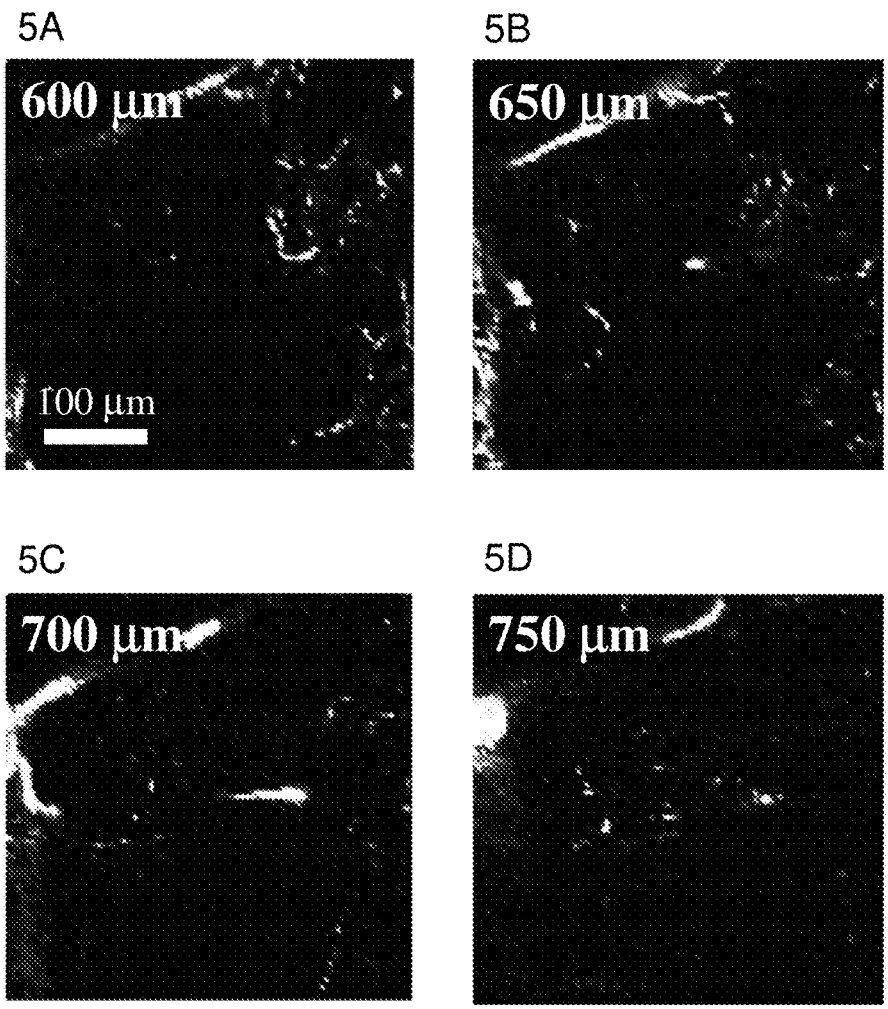
FIG. 5A-5H is a series of NIR images of a tumor, taken with the present confocal microscope. 5A-D shows confocal fluorescence images of an in vivo tumor sample resected from a tumor-bearing mouse with NIR-II fluorescent SWCNTs. 5A-D are typical NIR-II confocal fluorescence images of the tumor at different depths ranging from 600 μm to 750 μm. 5 E-H are 3D reconstructed images of the tumor sample, showing perspective views of the distribution of SWCNTs inside the tumor body. The white bar in FIG. 5A is a size bar indicating 100 μm. The tumor was fixed both chemically (with paraformaldehyde) and physically (with epoxy resin), and intra-tumorally injected with a solution of SWCNTs.
Figure 5E:
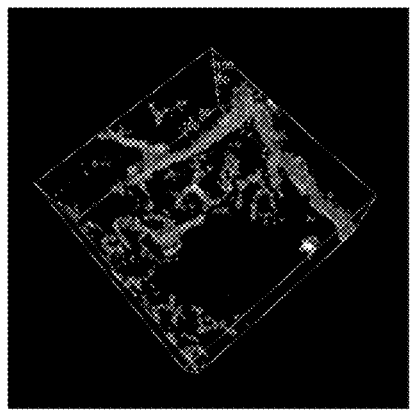
Figure 5F:
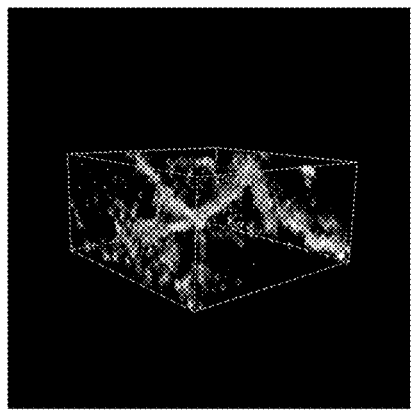
Figure 5G:
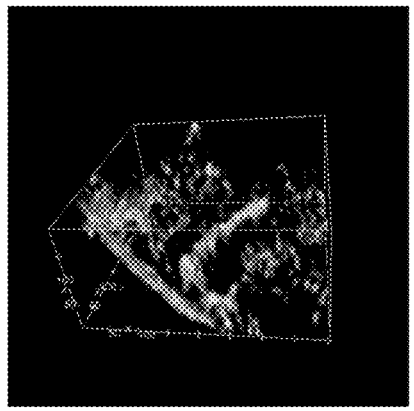
Figure 5H:
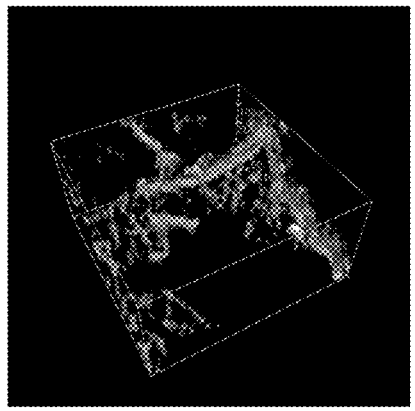

Using the system described above, we obtained confocal images of gold-coated glass fibers adsorbed with NIR-II fluorescent SWCNTs. FIG. 2 is a comparison between NIR-II widefield fluorescence images and NIR-II confocal fluorescence images, showing that throughout different depths of focus from 0 μm to 30 μm, the confocal system provides images of much higher clarity and resolution than the widefield system. FIG. 3A-3D shows example NIR-II confocal fluorescence images (A and B) and 3D reconstructions generated from such images (C and D).

NIR-II confocal fluorescence images were also obtained from tumors. NIR-II confocal fluorescence images from an ex vivo tumor sample injected with NIR-II fluorescent SWCNTs are shown in FIG. 4A-4I. FIG. 4A-4F shows confocal images of the tumor at different depths ranging from 0 mm to 3 mm. A 3D reconstruction of the tumor sample, showing the distribution of SWCNTs inside the tumor body, was generated. The 3D reconstruction is viewed from three different perspectives in FIG. 4G-4I. NIR-II confocal fluorescence images from an in vivo tumor sample are shown in FIG. 5A-5H. Confocal images of the tumor at different depths ranging from 600 μm to 750 μm are shown in FIGS. 5A-5D and 3D reconstructed images of the tumor are shown in FIG. 5E-5H.

As another example (image not shown), mouse brain has been reconstructed to obtain an image in both the x-y plane and an orthogonal view along the z direction. A few cerebral blood vessels were included in a smaller volume of 160 μm (x)×160 μm (y)×300 (z) with a voxel resolution of 4 μm×4 μm×4 μm for clarity reasons, revealing the expansion of the blood vessels in all directions of the 3D space. Voxel resolution as low as a voxel resolution of 3 μm×3 μm×3 μm has been demonstrated.

As another example (image not shown), a confocal image was obtained in high resolution (pixel size=4 μm), in the depth range of 800-1128 μm of an in vivo xenograft tumor inoculated into a nude mouse. The mouse was as injected with biocompatible SWNTs and imaged with NIR-II confocal microscope under anesthesia. 3D rendering of the SWNT-injected mouse xenograft tumor after image reconstruction from the high-resolution 2D slices were obtained, showing the bird's eye view, top view and side views of a scanned volume of 1200 μm (x)×876 μm (y)×328 μm (z) with a voxel resolution of 4 μm×4 μm×4 μm. The scan directions of all axes (x: fast axis in each 2D image; y: slow axis in each 2D image; z: depth axis of the 3D volume) were obtained. Renderings at 600 μm, 650 μm, 700 μm, and 750 m depth clearly show the tumor structure.

The present confocal microscope and method for use (data acquisition and manipulation) has been applied to an ex vivo heart as well (data not shown). Both 2D slices and 3D reconstruction from the NIR data by computed tomography were obtained in high resolution.

Example 3: Autofluorescence-Free Biological Imaging in the Long NIR Window (1500-1700 nm)

The instrument above can be used for autofluorescence-free biological imaging. Autofluorescence is the natural emission from biological structures upon light excitation and is problematic for fluorescence-based optical imaging.[19-27] The non-specific background caused by autofluorescence severely limits the imaging detection sensitivity by polluting the signal from the fluorescence contrast agents specifically localized in the area of interest.[28] Recently, we and others have discovered that by rejecting the autofluorescence emission below 1000 nm, the second near-infrared region (NIR-II, 1000-1700 nm) offers significantly reduced autofluorescence background compared to the visible and traditional near-infrared regions (400-900 nm).[1,2,7,8,29] However, to make NIR-II fluorescence imaging useful for clinical applications, reliable and unambiguous imaging results with "zero tissue autofluorescence" are highly desirable. We have discovered that fluorescence imaging in the long end of the NIR-II region (1500-1700 nm, named NIR-IIb region) minimizes the tissue autofluorescence and offers a novel "autofluorescence-free" NIR fluorescence window.

We first characterized the autofluorescence intensity from a mouse body and ex vivo liver sample when excited with an 808 nm laser diode upon various exposure times (FIG. 6A,6B). To compare the wavelength-dependent effects of tissue autofluorescence, three NIR emission subregions with different wavelength ranges are chosen, including NIR-II (1000-1700 nm), NIR-IIa (1300-1400 nm) and NIR-IIb (1500-1700 nm). An astoundingly high autofluorescence was detected from liver, intestine and bladder in the previously widely used NIR-II region, even upon a relatively short imaging exposure time. The autofluorescence level was remarkably reduced in the NIR-IIa region by avoiding the emission below 1300 nm, however, the intestinal and liver autofluorescence remained detectable. This autofluorescence level may be tolerable for low-resolution, high intensity fluorescence imaging, but will become significant when detecting relatively low signal from fluorescent contrast agents deep inside the body, for instance, molecular imaging from an imaging focal depth of a few millimeters. Consequently, NIR-IIb imaging with almost zero autofluorescence is highly desirable for improving detection sensitivity and specificity by avoiding the non-specific background emitted naturally from biological structures. This is thought to be the first NIR imaging window capable of offering autofluorescence-free imaging results without any post-imaging correction and removal.

Figure 7A:
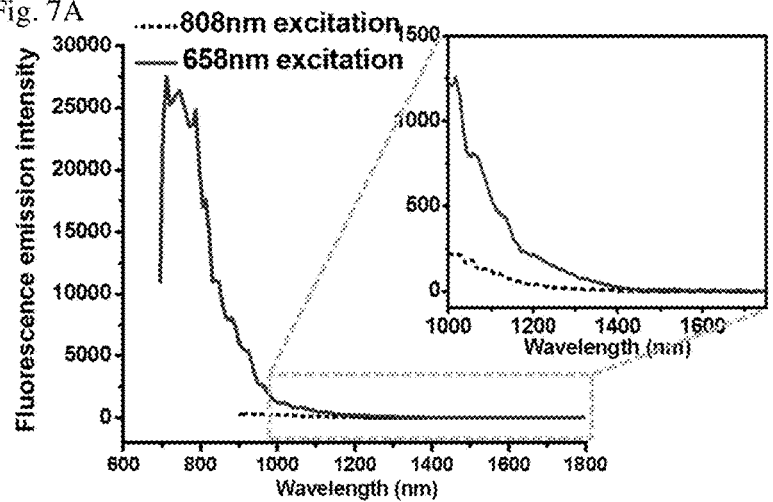
FIG. 7A-7C is a series of graphs that show autofluorescence emission spectra of a liver sample upon 658 nm and 808 nm excitation, with the line graph in (7A) showing the relation of fluorescence emission intensity vs. emission wavelength. Bar graphs in (7B) and (7C) show mean autofluorescence detected in different NIR regions upon excitation with 658 nm and 808 nm lasers, respectively.
Figure 7B:
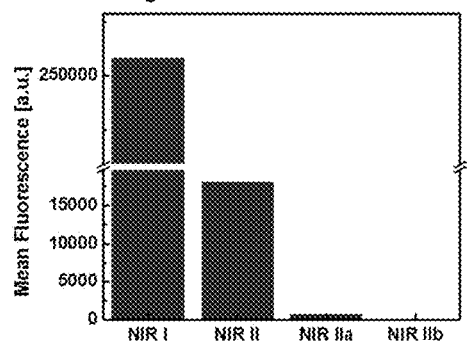
Figure 7C:
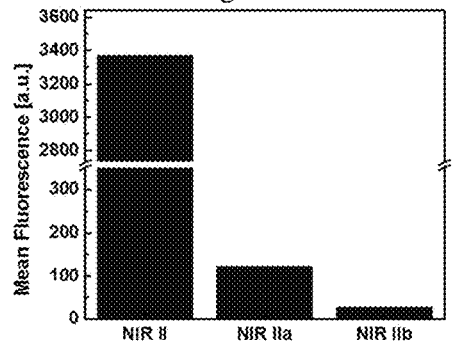

To further quantitatively confirm the trend that the autofluorescence decreases against emission wavelengths, we measured the autofluorescence emission spectra from a highly auto-fluorescent liver sample upon excitation with 658 nm and 808 nm lasers. It is clearly shown in FIG. 7A-7C that autofluorescence intensity decreases as the emission wavelength changes from NIR-I (750-900 nm) to NIR-IIb (1500-1700 nm) regions for both excitation lasers. A significant autofluorescence was observed for wavelengths below 1200 nm; however, the intensity drops to baseline beyond 1500 nm. By normalizing the power density of the two excitation lasers, we found that 808 nm excitation gives a much lower autofluorescence than 658 nm. As a result, the only NIR window that gives almost no autofluorescence is the one beyond 1500 nm when excited using an 808 nm laser.

FIG. 8A-8B further shows uses of the present device, namely the imaging of bending of cardiac microvessels in the same focal plane. FIG. 8A shows a high-resolution NIR-II confocal microscope image of the myocardium from an ex vivo heart sample perfused with SWCNTs. The scanned size is 1 mm×1 mm with a pixel size of 3 μm×3 μm, showing the bending of cardiac blood vessels within the same focal plane at the 1000 μm depth, as the cardiac vessels conform to the longitudinal direction of the cardiomyocytes. FIG. 8B is a close-up view of the blue box in FIG. 8A, showing minimum bending of cardiac blood vessels within a smaller field of view of 420 μm×450 μm.

Thus, using NIR-II detecting microscopes in wide field and confocal setups, we have shown that NIR-IIb fluorescence imaging is useful for minimizing the autofluorescence from biological structures. This unique optical property will enable NIR-IIb fluorescence imaging having high detection sensitivity with signal merely from pure fluorescent contrast agents, avoiding any pollution by non-specific background interference caused by autofluorescence.

In addition to liver samples, NIR-II confocal images have been obtained with high resolution in samples from the heart, and brain. Images have been used for determining vessel dimensions.

Example 4: Immunohistochemical (IHC) Staining and FISH (Fluorescence In Situ Hybridization) Assays by NIR-Confocal Imaging The NIR-II confocal microscope and NIR-II fluorophores above can be used for ex vivo tissue staining of protein biomarkers and nucleic acids. Single-walled carbon nanotubes (SWCNTs) can be used as near-infrared fluorophores for tissue and cellular imaging with minimal background autofluorescence. Conventional fluorophores emit in the visible, a region in which both tissues and cells exhibit high levels of autofluorescence arising from endogenous fluorophores such as elastin, collagen, and phenylalanine.[30] Many common tissue and cell culture imaging applications suffer from high levels of autofluorescence, making it difficult to extract useful information during imaging especially if trying to detect low intensity signals. Longer wavelengths provide less scattering coupled with minimal autofluorescence. SWCNTs in particular are ideal fluorophores for biological imaging with an emission range from 900 nm to 1700 nm. Furthermore, in the IIB region (1500 m to 1700 nm), tissues and cells exhibit near zero levels of autofluorescence and many common imaging substrates such as glass and certain plastics also show near zero levels of autofluorescence allowing for clear detection of small quantities of antigens. SWCNTs are coated with surfactants terminating with amine groups which provide an ideal scaffold for attaching antibodies such as anti-mouse IgG, commonly used as a secondary antibody or DNA/RNA probes.[31] Conjugating molecular probes to SWCNTs is a straightforward process involving sulfo-SMCC chemistry, and SWCNT conjugates are stable for long periods of time.[1]

Immunohistochemistry (IHC) is a staple imaging technique used for antigen detection in cells and tissue that could greatly benefit from the use of SWCNT fluorophores. Briefly, a primary antibody is applied that is specific for a protein of interest after which a secondary antibody coupled to a fluorophore is added that specifically binds to the primary antibody.[32] To date, all IHC performed has relied on fluorophores emitting in the visible region which makes it very difficult to detect fluorescent signals in organs such as the liver that exhibit high levels of autofluorescence. Furthermore, IHC is used in a clinical setting and the ability to detect weak fluorescent signals will enable the detection of low levels of disease markers in tissue sections.[33] While there are methods that will reduce the levels of background autofluorescence, they are tedious and will not result in the complete removal of endogenous autofluorescence. It would be much preferable to scan a slide or well plate post-staining and definitively conclude that any fluorescence arises from the presence of the antigen being detected. SWCNTs can be incorporated into standard protocols in place of conventional fluorophores which will allow for IHC in the near absence of autofluorescence. For instance, we have found that a JIB SWCNT-anti mouse IgG nanotube-antibody conjugate can be used for the detection of ALK, a lung cancer biomarker, with near zero background signal in lung biopsies from a human patient (data not shown). This signifies that, after an optimized protocol is applied, any positive signal must come from ALK+ tissue and that the minimum ALK marker detection is not limited by the autofluorescence levels.

Another commonly used biological imaging technique that could benefit from the use of SWCNT fluorophores is fluorescence in-situ hybridization (FISH). Fluorescence in-situ hybridization is used to detect DNA sequences on chromosomes or RNA expression levels within a cell.[34] The basic premise of this technique is to perform hybridization within a cell or tissue section, enabling visualization of where a gene sits within a chromosome or to determine if a gene is expressed, and if so, it enables spatial mapping of RNA/microRNA sequences within a cell. FISH has been previously performed with conventional fluorophores which emit in regions of high biological autofluorescence. Many applications are not realizable by using conventional fluorophores.[35] For instance, there is a growing interest in imaging RNA expression within the liver or primary cell cultures. Unfortunately, high levels of autofluorescence disallow FISH in either of these cases as FISH fluorescent signals are notoriously weak and even amplification methods cannot produce a strong enough signal in either liver sections or primary cells. For instance, it is not currently possible to perform FISH in liver sections that have been infected with hepatitis C to better study disease progression due to low fluorescent signals coupled with high background autofluorescence. We have found that SWCNTs can be used as fluorophores for FISH, generating FISH images that utilize a SWCNT-probe conjugate (data not shown). Similar to in IHC, SWCNTs can be incorporated into standard protocols and enable the detection of weak signals in a wide range of tissues in a way that is not currently realizable with our current array of visible fluorophores.

In addition, in the methods such as described in this example, said detecting comprises the use of a single point detector, and said methods further comprise one of: imaging of molecules treated within a single cell, imaging of a tissue, imaging of a labeled protein (including on antibody protein), nucleic acid imaging, and microarray imaging.

Imaging a microarray may be carried out, e.g. as described in Zhang et al. "An Integrated Peptide-Antigen Microarray on Plasmonic Gold Films for Sensitive Human Antibody Profiling," PLOS ONE 8(7): e71043. doi:10.1371/journal.pone.0071043 (Jul. 29, 2013). An array of biotinylated peptides were contacted with a primary antibody of interest; binding of the primary antibody was detected with a second antibody labeled with an NIR fluorophore (IRDye 800).

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

1. Welsher, K., et al. A route to brightly fluorescent carbon nanotubes for near-infrared imaging in mice. Nat Nanotechnol 4, 773-780 (2009).
2. Welsher, K., Sherlock, S. P. & Dai, H. J. Deep-tissue anatomical imaging of mice using carbon nanotube fluorophores in the second near-infrared window. Proceedings of the National Academy of Sciences of the United States of America 108, 8943-8948 (2011).
3. Hong, G. S., et al. Multifunctional in vivo vascular imaging using near-infrared II fluorescence. Nat Med 18, 1841-+(2012).
4. Naczynski, D. J., et al. Rare-earth-doped biological composites as in vivo shortwave infrared reporters. Nat Commun 4(2013).
5. Yi, H. J., et al. M13 Phage-Functionalized Single-Walled Carbon Nanotubes As Nanoprobes for Second Near-Infrared Window Fluorescence Imaging of Targeted Tumors. Nano Lett 12, 1176-1183 (2012).
6. Bashkatov, A. N., Genina, E. A., Kochubey, V. I. & Tuchin, V. V. Optical properties of human skin, subcutaneous and mucous tissues in the wavelength range from 400 to 2000 nm. J Phys D Appl Phys 38, 2543-2555 (2005).
7. Hong, G., et al. In Vivo Fluorescence Imaging with Ag2S Quantum Dots in the Second Near-Infrared Region. Angewandte Chemie 124, 9956-9959 (2012).
8. Tao, Z., et al. Biological Imaging Using Nanoparticles of Small Organic Molecules with Fluorescence Emission at Wavelengths Longer than 1000 nm. Angewandte Chemie (2013).
9. Hong, G. S., et al. Metal-Enhanced Fluorescence of Carbon Nanotubes. J Am Chem Soc 132, 15920-15923 (2010).
10. Tsyboulski, D. A., Bachilo, S. M. & Weisman, R. B. Versatile visualization of individual single-walled carbon nanotubes with near-infrared fluorescence microscopy. Nano Lett 5, 975-979 (2005).
11. Leeuw, T. K., et al. Single-walled carbon nanotubes in the intact organism: Near-IR imaging and biocompatibility studies in Drosophila. Nano Lett 7, 2650-2654 (2007).
12. Cognet, L., et al. Stepwise quenching of exciton fluorescence in carbon nanotubes by single-molecule reactions. Science 316, 1465-1468 (2007).
13. Reuel, N. F., Dupont, A., Thouvenin, O., Lamb, D. C. & Strano, M. S. Three-Dimensional Tracking of Carbon Nanotubes within Living Cells. Acs Nano 6, 5420-5428 (2012).
14. Hong, G. S., et al. Three-dimensional imaging of single nanotube molecule endocytosis on plasmonic substrates. Nat Commun 3(2012).
15. Hong, G. S., et al. Near-Infrared-Fluorescence-Enhanced Molecular Imaging of Live Cells on Gold Substrates. Angew Chem Int Edit 50, 4644-4648 (2011).
16. Zhang, Y., et al. Biodistribution, pharmacokinetics and toxicology of Ag2S near-infrared quantum dots in mice. Biomaterials 34, 3639-3646 (2013).
17. Nichols, A. J. & Evans, C. L. Video-rate scanning confocal microscopy and microendoscopy. Journal of visualized experiments: JoVE (2011).
18. Webb, R. H., Hughes, G. W. & Delori, F. C. Confocal scanning laser ophthalmoscope. Applied optics 26, 1492-1499 (1987).
19. Andersson-Engels, S., of Klinteberg, C., Svanberg, K. & Svanberg, S. In vivo fluorescence imaging for tissue diagnostics. Physics in medicine and biology 42, 815 (1997).
20. Frangioni, J. V. In vivo near-infrared fluorescence imaging. Current opinion in chemical biology 7, 626-634 (2003).
21. He, X., Gao, J., Gambhir, S. S. & Cheng, Z. Near-infrared fluorescent nanoprobes for cancer molecular imaging: status and challenges. Trends in molecular medicine 16, 574-583 (2010).
22. He, X., Wang, K. & Cheng, Z. In vivo near-infrared fluorescence imaging of cancer with nanoparticle-based probes. Wiley Interdisciplinary Reviews: Nanomedicine and Nanobiotechnology 2, 349-366 (2010).
23. Luo, S., Zhang, E., Su, Y., Cheng, T. & Shi, C. A review of NIR dyes in cancer targeting and imaging. Biomaterials 32, 7127-7138 (2011).
24. Ntziachristos, V., Bremer, C. & Weissleder, R. Fluorescence imaging with near-infrared light: new technological advances that enable in vivo molecular imaging. European radiology 13, 195-208 (2003).
25. Pinaud, F., et al. Advances in fluorescence imaging with quantum dot bio-probes. Biomaterials 27, 1679-1687 (2006).
26. Sevick-Muraca, E. Translation of near-infrared fluorescence imaging technologies: emerging clinical applications. Annual review of medicine 63, 217-231 (2012).
27. Wu, X., et al. Ultrasmall near-infrared gold nanoclusters for tumor fluorescence imaging in vivo. Nanoscale 2, 2244-2249 (2010).
28. Leblond, F., Davis, S. C., Valdes, P. A. & Pogue, B. W. Pre-clinical whole-body fluorescence imaging: Review of instruments, methods and applications. Journal of Photochemistry and Photobiology B: Biology 98, 77-94 (2010).
29. Welsher, K., Liu, Z., Daranciang, D. & Dai, H. Selective probing and imaging of cells with single walled carbon nanotubes as near-infrared fluorescent molecules. Nano letters 8, 586-590 (2008).
30. Banerjee B, Miedema B, Chandrasekhar HR. Emission spectra of colonic tissue and endogenous fluorophores. Am J Med Sci. 316(3), 220-6 (1998).
31. Buchwalow, I., Samoilova, V., Boecker, W., Tiemann, M. Non-specific binding of antibodies in immunohistochemistry: fallacies and facts. Scientific Reports 1, Article number: 28

32. Shi, S., Shi, Y., Taylor, C. R. Antigen Retrieval Immunohistochemistry: Review and Future Prospects in Research and Diagnosis over Two Decades. *J Histochem Cytochem* 59: 13 (2011)
33. Miettinen, M. Immunohistochemistry of soft tissue tumours—review with emphasis on 10 markers. *Histopathology* 64, 101-118, (2014)
34. Hicks, D. G., Tubbs, R. R., Assessment of the HER2 status in breast cancer by fluorescence in situ hybridization: a technical review with interpretive guidelines, *Human Pathology*, 36, 250-261 (2005)
35. an de Corput, M. P, Dirks, R. W., van Gijlswijk, R. P, van Binnendijk, E, Hattinger, C. M, de Paus, R. A, Landegent, J. E., Raap, A. K. Sensitive mRNA detection by fluorescence in situ hybridization using horseradish peroxidase-labeled oligodeoxynucleotides and tyramide signal amplification. *J Histochem Cytochem.* 46(11), 1249-59 (1998).

What is claimed is:

1. A near-infrared (NIR) confocal imaging device, comprising:
    (a) a light source constructed to illuminate a sample using an excitation light and to produce an emission light, from the sample, in a NIR range;
    (b) an optical path from the light source to and through an objective lens directed to the sample;
    (c) a detector constructed to detect NIR light at a wavelength between about 800 nm to 1700 nm;
    (d) a fixed beam splitter separating excitation light and emission light, wherein the emission light is directed to the detector;
    (e) a translational stage configured to support the sample and operative to cause a raster scanning movement relative to the objective lens during imaging and further comprising one or more actuators to move the translational stage in three dimensions during scanning; and
    (f) a computer comprising instructions which cause the confocal imaging device to:
        synchronize the scanning of the translational stage with the detector,
        detect emitted NIR light from the sample at a wavelength between about 800 nm to 1700 nm,
        move the translational stage in an x-y direction under control of the computer to obtain a raster scan of the sample,
        acquire data of individual pixels received by the detector at specified locations during scanning of the translational stage, and
        produce an image of the sample.
2. The device of claim 1, wherein the light source is one of a near infrared laser emitting at a selective wavelength between 800 nm and 1350 nm, and a laser emitting at a selected wavelength between 1350-1540 nm.
3. The device of claim 2 in a system with a sample, wherein the sample comprises a fluorophore that is (a) a NIR fluorescent dye, (b) a quantum dot, (c) a carbon nanostructure, or (d) a single-walled carbon nanotube (SWCNT) linked to a biological affinity molecule.
4. The device of claim 3 wherein the biological affinity molecule is an antibody.
5. The device of claim 1 wherein the optical path comprises a first structure that directs the excitation light to the fixed beam splitter that is a dichroic mirror and a second structure for receiving light from said objective lens, and wherein said dichroic mirror directs light though a pinhole structure to the detector, said first structure and second structure comprising light-exposed surfaces that do not absorb near-infrared light.
6. The device of claim 1 wherein the translational stage is constructed to cause movement relative to a fixed-position objective in x and y directions to form a raster scan and in a z direction to define a focal plane for light directed to the detector.
7. The device of claim 6 wherein the translational stage comprises x-y motion control at a rate of approximately 1 MHz.
8. The device of claim 1 wherein the detector is an InGaAs avalanche photodiode (APD) or photo-multiplier tube (PMT) with near-IR sensitivity.
9. A device according to claim 1 wherein said device computes image data to construct an NIR image in a dimension extending into the sample.
10. The device of claim 1, further comprising a mirror with a broad reflection band covering the NIR wavelength region between about 1000 nm to 1700 nm.
11. The device of claim 10, wherein the excitation light hits a center of the mirror.
12. The device of claim 1, wherein the excitation light and the emission light are configured to remain stationary during imaging.
13. A method for imaging a sample using a near infrared (NIR) confocal microscope, comprising:
    (a) positioning the sample on a translational stage;
    (b) exciting the sample through an objective lens with NIR light;
    (c) receiving emitted NIR light through the objective lens in a NIR wavelength;
    (d) directing received emitted NIR light to a NIR detector, wherein said detector is operatively connected to a computer, wherein said optical path does not require movement internally during above-recited steps of exciting, receiving, and directing;
    (e) detecting emitted NIR light from the sample at a NIR wavelength between about 800 nm to 1700 nm;
    (f) moving said translational stage in an x-y direction under control of said computer to obtain a raster scan of the sample;
    (g) either moving said translational stage in a z direction and synchronizing z direction movement with receiving light while moving in an x-y direction or holding said translational stage at a fixed z position; and
    (h) constructing light data, using said computer, to obtain an image of the sample.
14. The method of claim 13 wherein the imaging is an image of a cell, a tissue sample, or an ex vivo tumor sample.
15. The method of claim 13 wherein the image is obtained from a mammalian tissue and is constructed in a three dimensional reconstruction at a voxel resolution of less than 10 µm×10 µm×10 µm.
16. The method of claim 13 wherein exciting the sample is performed using a light source that is one of a laser emitting at a selective wavelength between 800 nm and 1350 nm, and a laser emitting at a selected wavelength between 1350-1540 nm.
17. The method of claim 16 wherein the sample is labeled with a NIR label.
18. The method of claim 16 wherein said translational stage moves in the x, y and z directions and a slice-by-slice image is produced.
19. The method of claim 13 wherein the translational stage is moved at a frequency of 0.5 to 1 MHz in the x, y and z directions.
20. The method of claim 13 wherein said NIR detector detects infrared light at the wavelength between about 800 nm to 1700 nm.

21. The method of claim 13 wherein said NIR detector detects infrared light at the wavelength between about 1300 nm to 1700 nm or between 1500-1700 nm.

22. The method of claim 13 wherein said NIR detector is an InGaAs detector, including an InGaAs avalanche photo-diode (APD) or photo-multiplier tube (PMT) having NIR sensitivity.

23. The method of claim 13 wherein said image is obtained from a depth of up to 5 mm in a biological tissue.

* * * * *